United States Patent [19]

Pierdet et al.

[11] 4,203,981
[45] May 20, 1980

[54] NOVEL 17 α-ARYL-STEROIDS

[75] Inventors: André Pierdet, Noisy-le-Sec; Vesperto Torelli, Maisons-Alfort; Roger Deraedt, Les Pavillons-sous-Bois, all of France

[73] Assignee: Roussel Uclaf, Paris, France

[21] Appl. No.: 692

[22] Filed: Jan. 3, 1979

[30] Foreign Application Priority Data

Jan. 11, 1978 [FR] France ............................ 78 00658

[51] Int. Cl.² ..................... C07J 23/00; A61K 31/56
[52] U.S. Cl. ......................... 424/243; 260/239.55 R; 260/397.45
[58] Field of Search .................. 424/243; 260/239.55, 260/397.45

[56] References Cited

U.S. PATENT DOCUMENTS 3,522,243  7/1970  Christiansen et al. ............ 260/239.5

Primary Examiner—Elbert L. Roberts
Attorney, Agent, or Firm—Hammond & Littell, Weissenberger & Muserlian

[57] ABSTRACT

Novel steroids of the formula

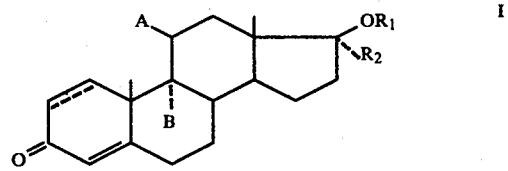

wherein $R_1$ is selected from the group consisting of hydrogen and acyl of an organic carboxylic acid of 1 to 18 carbon atoms, $R_2$ is selected from the group consisting of optionally substituted aryl of 6 to 12 carbon atoms and optionally substituted heterocyclic selected from the group consisting of furyl, thienyl, pyridyl and pyrimidyl, the optional substituents being selected from the group consisting of hydroxy, alkyl and alkoxy of 1 to 4 carbon atoms, halogens and —$CF_3$, the dotted line in the A ring indicates an optional $\Delta^{1(2)}$- double bond and A may be oxo and B is hydrogen or A is $\Delta$—OH and B is hydrogen or halogen or A and B form a $\Delta^{9(10)}$- double bond having very good anti-inflammatory activity and their preparation and novel intermediates.

37 Claims, No Drawings

NOVEL 17 α-ARYL-STEROIDS

STATE OF THE ART

U.S. Pat. No. 3,428,627 and Tetrahedron, Vol. 21 (1965), p. 1197–1202 describe 17α-heteroaryl-19-nor-steroids and French Pat. No. 1,360,436 and No. 1,046,040 describe 17α-phenyl and 17α-heteroaryl-androstanes.

OBJECTS OF THE INVENTION

It is an object of the invention to provide the novel steroids of formula I as well as a novel process for their preparation and novel intermediates therefore.

It is a further object of the invention to provide novel anti-inflammatory compositions and to a novel method of relieving inflammation in warm-blooded animals.

These and other objects and advantages of the invention will become obvious from the following detailed description.

THE INVENTION

The novel steroids of the invention have the formula

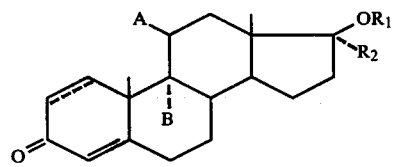

wherein $R_1$ is selected from the group consisting of hydrogen and acyl of an organic carboxylic acid of 1 to 18 carbon atoms, $R_2$ is selected from the group consisting of optionally substituted aryl or arylalkyl of 6 to 12 carbon atoms and optionally substituted heterocyclic selected from the group consisting of furyl, thienyl, pyridyl and pyrimidyl, the optional substituents being selected from the group consisting of hydroxy, alkyl and alkoxy of 1 to 4 carbon atoms, halogens and —$CF_3$, the dotted line in the A ring indicates an optional $\Delta^{1(2)}$-double bond and A may be oxo and B is hydrogen or A is β-OH and B is hydrogen or halogen or A and B form a $\Delta^{9(11)}$-double bond.

Examples of suitable carboxylic acids for the acyl $R_1$ are saturated or unsaturated aliphatic and cycloaliphatic carboxylic acids like alkanoic acids such as formic acid, acetic acid, propionic acid, butyric acid, isobutyric acid and undecylic acid; hydroxyl alkanoic acids such as hydroxy acetic acid; cycloalkyl carboxylic acids and cycloalkyl alkanoic acids such as cyclopropylcarboxylic acids, cyclopentylcarboxylic acid, cyclohexylcarboxylic acid, cyclopentylacetic acid, cyclohexylacetic acid, cyclopentylpropionic acid and cyclohexylpropionic acid; benzoic acid; phenylalkanoic acids such as phenylacetic acid and phenylpropionic acid; and amino acids such as diethylaminoacetic acid and aspartic acid.

Examples of suitable aryl and arylalkyl substituents of $R_2$ are phenyl and benzyl and the optional substituents may be in the ortho, meta or para positions and may be hydroxy, alkyl and alkoxy such as methyl or methoxy, halogens such as chlorine, fluorine or bromine or —$CF_3$ and any combination thereof.

Among the preferred compounds of formula I are those wherein $R_2$ is aryl, especially phenyl, those wherein $R_2$ is aralkyl, especially benzyl optionally substituted with —OH or —$CF_3$, those wherein $R_1$ is hydrogen, those wherein A is oxo and B is hydrogen, those wherein A is β—OH and B is hydrogen, those wherein A is β-OH and B is halogen, especially fluorine and those wherein A and B form a $\Delta^{9(11)}$ double bond as well as those wherein the A ring may or may not contain a $\Delta^{1(2)}$-double bond. Especially preferred is 17α-o-hydroxyphenyl-$\Delta^{1,4}$-androstadiene-11β, 17β-diol-3-one.

The novel process of the invention for preparation of compounds of formula I comprises reacting a compound of the formula

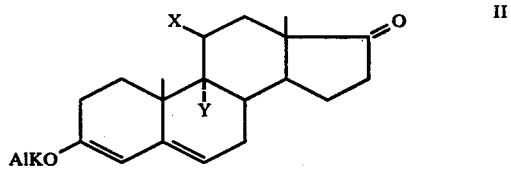

wherein AlK is alkyl of 1 to 6 carbon atoms and X is oxo and Y is hydrogen or X and Y form a $\Delta^{9(11)}$-double bond with a compound of the formula $R_2$—Li wherein $R_2$ has the above definition and then with a hydrolysis acid agent to obtain a compound of the formula.

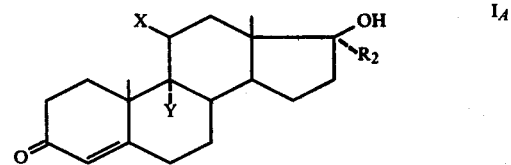

which may when X is oxo and Y is hydrogen be reacted with an alkyl orthoformate in an acid medium and then with a reducing agent followed by acid hydrolysis to obtain a compound of the formula

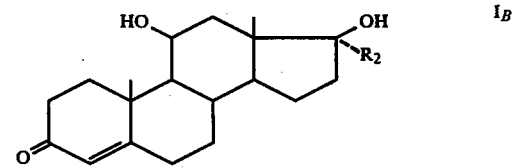

or when X and Y are a $\Delta^{9(11)}$-double bond be reacted with N-bromosuccinimide in the presence of perchloric acid to obtain a compound of the formula

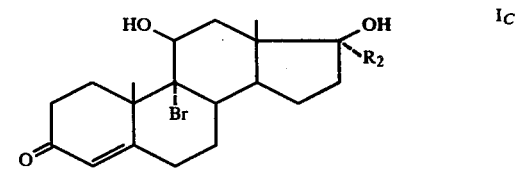

which may be reacted with a basic agent to obtain a compound of the formula

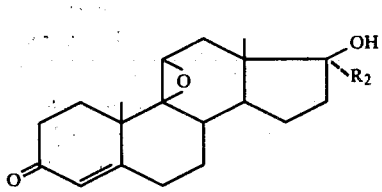

which is then reacted with H-Hal wherein Hal is chlorine or fluorine to obtain a compound of the formula

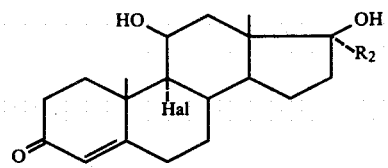

and the compounds of formulae $I_A$, $I_B$, $I_C$ and $I_D$ may be reacted with a deshydrogenation agent to obtain the corresponding $\Delta^{1,4}$ compounds and the compounds of formula I wherein $R_1$ is hydrogen may be reacted with a selective esterification agent to obtain the corresponding compounds of formula I wherein $R_1$ is acyl.

In a preferred mode of the process of the invention, the reaction of the compound of formula II and $R_2Li$ is effected in ether, tetrahydrofuran or mixtures thereof and the acid hydrolysis agent is hydrochloric acid, sulfuric acid, acetic acid, citric acid or p-toluene sulfonic acid and the hydrolysis is effected in one or more solvents such as alcohols like methanol, ethanol and isopropanol or ketones such as acetone.

The alkyl orthoformate is preferably methyl orthoformate or ethyl orthoformate and the reducing agent is preferably an alkali metal borohydride like sodium borohydride or potassium borohydride or a mixed hydride such as lithium aluminum hydride. The basic agent used to treat the compounds of formula $I_C$ are preferably an alkali metal hydroxide such as potassium hydroxide or sodium hydroxide or an alkali metal alcoholate such as sodium methylate or sodium ethylate. The compounds of formulae $I_A$, $I_B$, $I_C$ or $I_D$ may have a double bond introduced in the 1(2)-position biochemically such as with arthrobacter simplex or with p-benzoquinone derivatives such as 2,3-dichloro-5,6-dicyanobenzoquinone. The esterification agent is preferably the acid anhydride or the acid chloride and is effected in the presence of an acid catalyst.

The compounds of formula II are generally known and may be prepared by the process of U.S. Pat. No. 3,055,917.

The novel intermediates of the invention 3-alkoxy-$\Delta^{3,5,9(11)}$-androstatriene-17-ones, especially 3-ethoxy-$\Delta^{3,5,9(11)}$-androstatriene-17-one and may be prepared by reacting alkyl orthoformates with $\Delta^{4,9(11)}$-androstadiene-3,17-dione to form the 3-alkoxy-66 $^{3,5,9}$(11)-androstatriene-17-ones.

In a variation of the process of the invention, the compounds of formula III may be prepared by reacting a compound of the formula

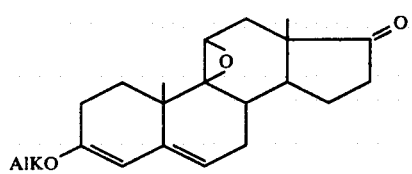

wherein AlK is alkyl of of 1 to 6 carbon atoms with a compound of the formula $LiR_2$ and then with an acid hydrolysis agent. The $R_2Li$ reaction is preferably effected as before with $R_2Li$ and a compound of formula II.

The compounds of formula IV, especially 3-ethoxy-$9\beta,11\beta$-epoxy-$\Delta^{3,5}$-androstadiene-17-one, are new compounds and may be prepared by reacting an alkyl orthoformate with $9\beta,11\beta$-epoxy-$\Delta^4$-androstene-3,17-dione described in U.S. Pat. No. 3,072,643.

The novel anti-inflammatory compositions of the invention are comprised of an anti-inflammatorily effective amount of at least one compound of formula I and an inert pharmaceutical carrier or excipient. The compositions may be in the form of tablets, dragees, gelules, granules, suppositories, injectable solutions or suspensions, pomades, cremes or aerosols prepared in the usual manner. Especially useful are compositions containing $17\beta$-o-hydroxyphenyl-$\Delta^{1,4}$-androstadiene-$11\beta,17\beta$-diol-3-one.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of rheumatism affections, arthroses, lombalgia, sciatics, nevralgia, myalgia or dental pain.

The novel method of the invention of relieving inflammation in warm-blooded animals, including humans, comprises administering to warm-blooded animals an anti-inflammatorily effective amount of at least one compound of formula I. The compounds may be administered orally, rectally or parenterally or topically to be skin or mucous. The usual daily dose is 0,1 to 2 mg/kg depending on the specific compound and method of administration.

In the following examples there are described several preferred embodiments to illustrate the invention. However, it is to be understood that the invention is not intended to be limited to the specific embodiments.

EXAMPLE 1

17α-o-hydroxyphenyl-$\Delta^4$-androstene-17$\beta$-ol-3,11-dione 26.8 g of o-bromophenol were added under a dry inert atmosphere to 360 ml of anhydrous ether and 180 ml of a 2 M solution of butyllithium in hexane was added dropwise at $-5°$ C. with stirring. The mixture was refluxed for one hour and after cooling to $-20°$ C., 30.8 g of 3-ethoxy-$\Delta^{3,5}$-androstadiene-11,17-dione were added thereto over 20 minutes. The temperature returned to room temperature over one hour and the mixture was poured into an ice-water mixture. Hydrochloric acid was added thereto and the mixture was extracted with ethyl acetate. The organic extracts were washed with water, dried and evaporated to dryness. The oily residue was dissolved in 200 ml of absolute ethanol and the solution together with 40 ml of N sulfuric acid was heated at 60° C. for 20 minutes. The mixture was cooled and diluted with water and was then extracted with ethyl acetate. The extract was dried and was chromatographed over silica gel. Elution with an 8-2 benzene-ethyl acetate mixture yielded 14.2 g of product which was crystallized from aqueous ethanol. The mixture was iced and vacuum filtered and the product was washed with 50% aqueous ethanol and was dried to obtain 10.78 g of pure 17α-o-hydroxyphenyl-$\Delta^4$-androstene-17β-ol-3,11-dione melting at 295° C.

Analysis: $C_{25}H_{30}O_4$; molecular weight=394.51. Calculated: %C 76.11; %H 7.66. Found: %C 76.1; %H 7.7.

IR Spectrum (chloroform): absorptions at 1709 cm$^{-1}$ (C=O); at 1670 cm$^{-1}$ (conjugated C=O); at 1619 cm$^{-1}$ (C=C); at 1584 and 1491 cm$^{-1}$ (aromatic ring); and at 3564 cm$^{-1}$ (OH).

| UV Spectrum (ethanol): | |
|---|---|
| Max. at 228 nm | $\epsilon = 15,900$ |
| Max. at 238 nm | $\epsilon = 15,800$ |
| Max. at 274 nm | $\epsilon = 2,760$ |
| Inflex. towards 280 nm | |
| Inflex. towards 310 nm | |

EXAMPLE 2

17α-o-hydroxyphenyl-$\Delta^4$-androstene-11β, 17β-diol-3-one

A mixture of 2.53 g of the product of Example 1, 2.5 ml of ethyl chloroformate and 25 ml of ethanol was heated to reflux and 0.5 ml of a solution of 0.2 ml of sulfuric acid in 100 ml of ethanol was added thereto. The mixture was stirred for 3 minutes after which 1 ml of pyridine was added thereto and the mixture was cooled and diluted with water. The mixture was extracted with chloroform and the organic phase was washed with water, dried and evaporated to dryness under reduced pressure to obtain 3-ethoxy-17α-o-hydroxyphenyl-$\Delta^{3,5}$-androstadiene-17β-ol-11-one in the form of a resin.

The said raw product was dissolved in 10 ml of ethanol and 4 ml of 2 N sodium hydroxide solution and after the addition of 5 g of sodium borohydride thereto, the mixture was refluxed for 4 hours and was cooled. The mixture was poured into ice water containing hydrochloric acid and the mixture was extracted with chloroform. The organic phase was washed with water, dried and evaporated to dryness under reduced pressure. The residue and 20 ml of ethanol and 5 ml of 2 N hydrochloric acid was heated at 45° C. for 10 minutes and then 1 g of sodium acetate and 2 g of acetic acid were added thereto. The mixture was held at 40° C. for 15 minutes and was then diluted with water and was extracted with chloroform. The organic phase was washed with water and evaporated to dryness. The dry residue was chromatographed over silica gel and elution with a 7-3 benzene-ethyl acetate mixture yielded 2.1 g of 17α-o-hydroxyphenyl-$\Delta^4$-androstene-11β, 17β-diol-3-one melting at 276° C. after crystallization from isopropanol.

Analysis: $C_{25}H_{32}O_4$; molecular weight=396.53. Calculated: %C 75.72 %H 8.13. Found: %C 75.8 % H 8.2.

IR Spectrum (chloroform): absorption at 3608 cm$^{-1}$ and 3580 and 3300 cm$^{-1}$ (OH)

| UV Spectrum (ethanol): | |
|---|---|
| Inflex. towards 228 nm | $\epsilon = 13,600$ |
| Max. at 241-242 nm | $\epsilon = 15,300$ |
| Inflex. towards 272 nm | |
| Inflex. towards 280 nm | |
| Inflex. towards 305 nm | |

EXAMPLE 3

17α-o-hydroxyphenyl-$\Delta^{1,4}$-androstadiene-11β, 17β-diol-3-one 15 g of arthrobacter simplex (powder ATCC 6946) and 1.5 g of diatomaceous silica were added to 750 ml of a solution buffered to a pH of 7 containing 9.6 g of monopotassium phosphate, 32 ml of sodium hydroxide solution and 1400 ml of water and then a solution of 780 mg of the product of Example 2 in 15 ml of methanol was added thereto. Air was bubbled through the mixture at 35° C. for 40 hours and the mixture was then filtered. The filtrate was extracted with chloroform and the organic phase was washed with water, dried and evaporated to dryness. The dry crystalline residue was chromatographed over silica gel and was eluted with chloroform containing 2% of methanol to obtain 480 mg of product. The latter was crystallized from a methylene chloride-isopropyl ether mixture to obtain 17α-o-hydroxyphenyl —$\Delta^{1,4}$-androstadiene-11β,17β-diol-3-one melting at 264° C.

Analysis: $C_{25}H_{30}O_4$; molecular weight =394.51. Calculated: %C 76.11 %H 7.66. Found: % C 76.1 %H 7.8.

IR Spectrum (chloroform): absorption at 1663 cm$^{-1}$ (C=O); at 1623, 1606 and 1583 cm$^{-1}$ (C=C); at 3606 and 3587 cm$^{-1}$ (OH).

| UV Spectrum (ethanol): | |
|---|---|
| Max. at 225 nm | $\epsilon = 13,400$ |
| Max. at 243 nm | $\epsilon = 14,250$ |
| Inflex. towards 308 nm | |

EXAMPLE 4

17α-phenyl-$\Delta^{4,9(11)}$-androstadiene-17β-ol-3-one

STEP A: 3-ethoxy-$\Delta^{3,5,9}$(11)-androstatriene-17-one 60 ml of ethyl chloroformate were added to a mixture of 22.08 g of $\Delta^{4,9(11)}$-androstadiene-3,17-dione in 74 ml of ethanol and the mixture was heated at 75° C. until dissolution occured. Then, 28.6 ml of an ethanol solution containing 18.4 mg of p-toluene sulonic acid were added thereto and the mixture was stirred for 3 minutes after which 3.7 ml of triethylamine were added thereto. The mixture was cooled and was diluted with water and was then extracted with methylene chloride. The organic phase was dried over sodium sulfate and was evaporated to dryness. The dry residue was chromatographed over silica gel and was eluted with a 9-1 cyclohexane-ethyl acetate mixture containing 0.1% of triethylamine to obtain 18.8 g of crystalline 3-ethoxy-$\Delta^{3,5,9(11)}$-androstatriene-17-one melting at 131° C.

IR Spectrum (chloroform): 1736 cm$^{-1}$ (C=O).

| UV Spectrum (ethanol): | |
| --- | --- |
| max. at 241 nm | $\epsilon = 16{,}200$ |

STEP B:
3-ethoxy-17α-phenyl-Δ$^{3,5,9(11)}$-androstatriene-17β-ol

A mixture of 4.7 ml of phenyllithium titering 1.37 moles/l and 25 ml of ether was heated to reflux and 500 mg of the product of Step A were added thereto. The mixture was refluxed under an inert atmosphere with stirring for 90 minutes and then 13.6 ml of ether saturated with water were added thereto. The mixture was stirred for 25 minutes and then another 4.7 ml of phenyllithium were added thereto. The mixture was stirred for one hour and another 10 ml of ether saturated with water were added. The mixture was stirred for another 15 minutes after which 14 ml of phenyllithium were added. The mixture was stirred for one hour and was cooled and the aqueous ammonium chloride solution was added thereto. The organic phase was washed with water, dried and evaporated to dryness under reduced pressure to obtain 1.9 g of 3-ethoxy-17α-phenyl-Δ$^{3,5,9(11)}$-androstatriene-17β-ol.

STEP C:
17α-phenyl-Δ$^{4,9(11)}$-androstadiene-17β-ol-3-one

A mixture of 1.9 g of the product of Step B, 19 ml of ethanol and 1.9 ml of N sulfuric acid was heated at 60° C. under an inert atmosphere for 30 minutes and was then cooled and neutralized with aqueous sodium bicarbonate solution. The mixture was extracted with methylene chloride and the organic phase was washed with a saturated aqueous sodium chloride solution, dried and evaporated to dryness. The residue was added to 5 ml of isopropyl ether and the mixture was iced and vacuum filtered. The recovered product was washed with isopropyl ether and was dried to obtain 360 mg of 17α-phenyl-Δ$^{4,9(11)}$-androstadiene-17β-ol-3-one melting at 244° C. The mother liquors were chromatographed over silica gel and elution with an 8-2 benzene-ethyl acetate mixture and crystallization from isopropyl ether yielded another 93 mg of the said product melting at 244° C.

IR Spectrum (chloroform): absorptions at 1663 cm$^{-1}$ (C=O); at 1613 and 1593 (C=C); and at 3593 cm$^{-1}$ (OH)

EXAMPLE 5
17α-o-hydroxyphenyl-Δ$^{4,9(11)}$-androstadiene-17β-ol-3-one

STEP A:
3-ethoxy-17α-o-hydroxyphenyl-Δ$^{3,5,9(11)}$-androstatriene-17β-ol

A mixture of 24 g of o-bromophenol and 480 ml of ether was cooled with stirring under an inert atmosphere to 0° to 5° C. and 171 ml of a hexane solution titering 1.55 moles/l of butyllithium was added thereto over 10 minutes. The mixture was refluxed for one hour and cooled to obtain a lithium containing solution of 0.20 moles/liter. 90 ml of the said solution were heated to reflux and a solution of 1.4 g of 3-ethoxy-Δ$^{3,5,9(11)}$-androstatriene-17-one in 18 ml of ether were added thereto. The mixture was refluxed under an inert atmosphere for 90 minutes and then 56 ml of ether saturated with water was added twice thereto. The mixture was stirred for 10 minutes and another 90 ml of the lithium containing solution were added thereto. The mixture was stirred for 45 minutes and 28 ml of ether saturated with water were added thereto. After stirring the mixture for 10 minutes, another 180 ml of lithium containing solution were added thereto and the mixture was refluxed with stirring for 15 hours. The mixture was then cooled to 0° to 5° C. and 100 ml of a saturated aqueous ammonium chloride solution were added thereto. The organic phase was washed with water, dried over sodium sulfate and evaporated to dryness at 40° C. under reduced pressure to obtain 14 g of 3-ethoxy-17α-o-hydroxyphenyl-Δ$^{3,5,9(11)}$-androstatriene-17β-ol in the form of an oil.

STEP B:
17α-o-hydroxyphenyl-Δ$^{4,9(11)}$-androstadiene-17β-ol-3-one

A mixture of the product of Step A, 70 ml of ethanol and 14 ml of N sulfuric acid was heated at 60° C. with stirring under an inert atmosphere for 30 minutes and after cooling the mixture, 20 ml of a saturated aqueous sodium bicarbonate solution were added thereto. 50 ml of ethyl acetate were added thereto and the decanted organic phase was washed with a saturated aqueous sodium chloride solution, was dried and evaporated to dryness to obtain 10.7 g of raw product. The latter was chromatographed over silica gel and was eluted with benzene and then with an 8-2 benzene-ethyl acetate mixture. The product was added to 8 ml of benzene and the mixture was vacuum filtered. The product was washed with benzene and dried to obtain 1.03 g of pure 17α-o-hydroxyphenyl-Δ$^{4,9(11)}$-androstadiene-17β-ol-3-one melting at ≃260° C. and a specific rotation of $[\alpha]_D^{20} = 148° \pm 3°$ (c=0.5% in chloroform). Chromatography of the mother liquid over silica gel and elution with a 9-1 benzene-ethyl acetate mixture yielded 120 mg more of the pure product melting at 260° C.

Analysis: C$_{25}$H$_{30}$O$_3$; molecular weight=378.49. Calculated: %C 79.32 %H 7.98. Found: %C 79.0 %H 8.00.

IR Spectrum (chloroform): absorption at 3610 and 3580 cm$^{-1}$ (OH); conjugated system+aromatic at 1665 cm$^{-1}$ (C=O) and at 1618, 1582 and 1490 cm$^{-1}$ (C=C).

| UV Spectrum (ethanol): | | |
| --- | --- | --- |
| Inflex. towards 230 nm | $E_1^1 = 379$ | |
| Max. at 239 nm | $E_1^1 = 405$ | $\epsilon = 15{,}300$ |
| $\|\alpha\|^{20} = +148° \pm 3°$ (C = 0,5% in chloroform). | | |

EXAMPLE 6
9α-fluoro-17α-o-hydroxyphenyl-Δ$^4$-androstene-11β,17β-diol-3-one

STEP A:
3-ethoxy-9β,11β-epoxy-Δ$^{3,5}$-androstadiene-17-one

A mixture of 20 g of 9β, 11β-epoxy-Δ$^4$-androstene-3,17-dione, 54 ml of ethyl orthoformate and 66 ml of ethanol was heated at 72°-74° C. until dissolution occured and 60 ml of an ethanol solution of 0.08% p-toluene sulfonic acid was added thereto 3 times at 5 minutes intervals at 72°-74° C. The mixture was cooled and 2 ml of triethylamine were added thereto. The mixture was poured into water and the mixture was extracted with methylene chloride. The organic phase was washed with a saturated aqueous sodium chloride solution, dried over sodium sulfate and evaporated to dryness under reduced pressure at 40° C. The residue was chromatographed over silica gel and was successively eluted with an 8-2 Essence B (b.p.=60°-80° C.)-benzene mixture containing 1% of triethylamine, a 6-4 Essence B-benzene mixture containing 1% of triethylamine and a 2-8 Essence B-benzene mixture containing 1% of triethylamine to obtain 15.5 g of pure 3-ethoxy-9β,11β-epoxy-Δ$^{3,5}$-androstadiene-17-one.

IR Spectrum (chloroform): absorption at 1740 cm$^{-1}$ (C=O); at 1652 and 1628 cm$^{-1}$ (Δ$^{3,5}$+3-ethoxy).

STEP B:
9β,11β-epoxy-17α-o-hydroxyphenyl-Δ$^4$-androstene-17β-ol-3-one

A solution of 4.5 g of the product of Step A in 45 ml of anhydrous ether was added under an inert atmosphere to a refluxing lithium containing solution of Step B in Example 4 and the mixture was refluxed for one hour leading to alternate successive protonations as follows: addition of 171 ml of ether saturated with water, reflux for 10 minutes, addition of 351 ml of lithium containing solution, reflux for 45 minutes, addition of 86 ml of ether saturated with water, reflux for 10 minutes, addition of 334 ml of lithium containing solution and reflux for 15 hours. The mixture was then iced and 300 ml of a saturated aqueous ammonium chloride solution were added thereto. The decanted organic phase was washed with water, with a saturated aqueous sodium chloride solution, dried and evaporated to dryness to obtain 15 g of 3-ethoxy-9β,11β-epoxy-17α-o-hydroxyphenyl-Δ$^{3,5}$-androstadiene-17β-ol.

A mixture of the said product, 75 ml of ethanol and 15 ml of N sulfuric acid was heated under an inert atmosphere with stirring at 60° C. for 30 minutes and the mixture was cooled and poured into 100 ml of a saturated aqueous sodium bicarbonate solution. 100 ml of ethyl acetate were added thereto and the decanted organic phase was washed with a saturated aqueous sodium chloride solution, was dried and evaporated to dryness under reduced pressure to obtain 14.3 g of raw product. The latter was chromatographed over silica gel and was successively eluted with benzene and then an 8-2 benzne-ethyl acetate mixture to obtain a crystalline product which was crystallized from benzene to obtain 2.93 g of 9α, 11β-epoxy-17α-o-hydroxyphenyl-Δ$^4$-androstene-17β-ol-3-one. The mother liquors were chromatographed over silica gel and elution with a 7-3 benzene-ethyl acetate mixture followed by crystallization from benzene yielded another 0.32 g of the said product melting at 170° C.

IR Spectrum (chloroform): absorption at 3608 and 3576 cm$^{-1}$ (OH); at 1584 and 1490 cm$^{-1}$ (aromatic); at 1622 cm$^{-1}$ (C=C); and at 1669, 1662 and 1651 cm$^{-1}$ (Δ$^4$-3-one).

| UV Spectrum (ethanol): | | |
|---|---|---|
| Max. at 225 nm | $E_1^1 = 270$ | |
| Max. at 244-245 nm | $E_1^1 = 352$ | $\epsilon = 13,900$ |
| Inflex. towards 279 nm | $E_1^1 = 60$ | |

STEP C:
9α-fluoro-17α-o-hydroxyphenyl-Δ$^4$-androstene-11β,17β-diol-3-one 5.77 g of the product of Step A were added over 5 minutes with stirring to 11.5 ml of a HF-dimethylformamide complex cooled to −35° C. and the mixture was stirred for 25 minutes and was poured into 200 ml of a mixture of ice-water and 35 ml of ammonium hydroxide. The mixture was stirred for 30 minutes and was vacuum filtered. The recovered product was washed with water until the wash water was neutral and dried to obtain 5.83 g of raw product. The product was added to 20 ml of methylene chloride and the mixture was refluxed for 15 minutes and was cooled. The mixture was vacuum filtered and the recovered product was washed with methylene chloride and was dried to obtain 4.05 g of pure 9α-fluoro-17α-o-hydroxyphenyl-Δ$^4$-androstene-11β,17β-diol-3-one melting at 262° C. which after crystallization melted at 195° C. (Maquenne block) and had a specific rotation of $[\alpha]_D^{20} = +125° \pm 3.5°$ (c=0.6% in ethanol).

Analysis: C$_{25}$H$_{31}$O$_4$F: molecular weight=414.50. Calculated: %C 72.43 %H 7.47 %F 4.58. Found: %C 72.5 %H 7.6 %F 4.5.

| UV Spectrum (ethanol): | | |
|---|---|---|
| Inflex. towards 230 nm | $E_1^1 = 342$ | |
| Inflex. towards 240 nm | $E_1^1 = 368$ | $\epsilon = 15,250$ |
| Max. at 273 nm | $E_1^1 = 56$ | $\epsilon = 2,300$ |
| Inflex. towards 278 nm | $E_1^1 = 50$ | |

| UV Spectrum (ethanol/0.1N NaOH): | |
|---|---|
| Max. at 241 nm | $\epsilon = 22,300$ |
| Max. at 293 nm | $\epsilon = 3,800$ |

IR Spectrum (Nujol): conjugated system+aromatic-—absorptions at 1657 cm$^{-1}$ (C=O); at 1619, 1580 and 1495 cm$^{-1}$ (C=C); at 3531 cm$^{-1}$ (OH).

EXAMPLE 7
9α-fluoro-17α-o-hydroxyphenyl-Δ$^{1,4}$-androstadiene-11β,17β-diol-3-one 11.2 ml of 10 N sodium hydroxide solution were added to a solution of 27.6 g of monobasic potassium phosphate in 3.95 liters of distilled water to adjust the pH to 7 and a solution of 3.4 g of 9α-fluoro-17α-o-hydroxyphenyl-Δ$^4$-androstene-11β,17β-diol-3-one in 184 ml of methanol were added to 7.1 liters of the resulting solution at 42° C. Air was lightly bubbled through the mixture at 42° C. and 3 times 24 g of diatomaceous silica and 24 g of arthrobacter simplex (powdered ATCC 6946) were added thereto. The mixture was stirred for 30 hours after the first introduction, 100 hours after the second introduction and 18 hours after the third introduction. The mixture was filtered and the filtrate was extracted with ethyl acetate and then with methylene chloride. The combined organic phases were dried over sodium sulfate and evaporated to dryness under reduced pressure. The residue was added to 15 ml of methylene chloride and the mixture was vacuum filtered. The product was washed with methylene chloride and dried to obtain 2.22 g of product. The latter was chromatographed over silica gel and was eluted with a 90-10-1 chloroform-dioxane-methanol mixture. The product was crystallized from methylene chloride to obtain 1.61 g of 9α-fluoro-17α-o-hydroxyphenyl-Δ$^{1,4}$-androstadiene-11β,17β-diol-3-one melting at 208° C. and having a specific rotation of $[\alpha]_D^{20} = +134° \pm 3°$ (c=0.5% in ethanol).

Analysis: $C_{25}H_{29}O_4F$: molecular weight=412.48. Calculated: %C 72.79 %H 7.08 %F 4.60. Found: %C 72.9 %H 7.1 %F 4.8.

| UV Spectrum (ethanol): | | |
| --- | --- | --- |
| Max. at 226 nm | $E_1^1 = 350$ | $\epsilon = 14,400$ |
| Max. at 238 nm | $E_1^1 = 354$ | $\epsilon = 14,600$ |
| Inflex. towards 270 nm | $E_1^1 = 153$ | $\epsilon = 6,300$ |
| Inflex. towards 280 nm | $E_1^1 = 84$ | $\epsilon = 3,500$ |

IR Spectrum (Nujol): conjugated system—absorption at 1658 cm$^{-1}$ (C=O) and at 1613, 1600 and 1580 cm$^{-1}$ (C=C); at 886 cm$^{-1}$ ($\Delta^{1,4}$-3-one).

EXAMPLE 8

9α-bromo-17α-phenyl-$\Delta^4$-androstene-11β,17β-diol-3-one 4.36 g of N-bromosuccinimide and 6.83 g of 17α-phenyl-$\Delta^{4,9(11)}$-androstadiene-11β-ol-3-one were added under an inert atmosphere to 103 ml of anhydrous acetone at 0° to 5° C. and after the temperature rose to 5° to 10° C., a solution of 21 ml of water and 4.36 ml of 55° Be perchloric acid were added thereto over 25 minutes. The mixture was stirred for 10 minutes and was diluted with 200 ml of water. The mixture was vacuum filtered and the recovered product was washed with water until the wash water was neutral to obtain 9α-bromo-17α-phenyl-$\Delta^4$-androstene-11β,17β-diol-3-one.

EXAMPLE 9

9α-fluoro-17α-phenyl-$\Delta^4$-androstene-11β,17β-diol-3-one

STEP A: 9β,11β-epoxy-17α-phenyl-$\Delta^4$-androstene-17β-ol-3-one

A mixture of the product of Example 8, 41 ml of methanol and 27.5 ml of methanolic N potassium hydroxide solution was stirred under an inert atomsphere at 20°–25° C. for 90 minutes and was then cooled and diluted with 150 ml of ice-water. The mixture was vacuum filtered and the recovered product was washed with water until the wash water was neutral to obtain 6.14 g of raw product. The latter was added to 150 ml of isopropanol and the mixture was refluxed until dissolution occured. The solution was filtered hot and was concentrated to 100 ml and iced. The mixture was vacuum filtered and the product was washed with iced propanol and dried to obtain 4.277 g of pure 9β,11βepoxy-17α-phenyl-$\Delta^4$-androstene-17β-ol-3-one melting at 216° C. and having a specific rotation of $[\alpha]_D^{20}=+3°\pm2°$ (c=0.5% in chloroform). A second crop of 0.793 g of the product was obtained from the mother liquors.

| UV Spectrum (ethanol): | | |
| --- | --- | --- |
| Inflex. towards 215 nm | $E_1^1 = 268$ | |
| Inflex. towards 220 nm | $E_1^1 = 245$ | |
| Max. at 244–245 nm | $E_1^1 = 367$ | $\epsilon = 13,900$ |

IR Spectrum (chloroform): absorption at 3595 cm$^{-1}$ (OH); at 1660 cm$^{-1}$ (C=O); at 1619 cm$^{-1}$ (C=C); at 865 cm$^{-1}$ (C—H of $\Delta^4$ and epoxy); and at 1600–1492 cm$^{-1}$ (aromatic).

STEP B:
9α-fluoro-17α-phenyl-$\Delta^4$-androstene-11β,17β-diol-3-one 11.4 g of the product of Step B were added under an inert atmosphere to 18.8 ml of a HF-dimethylformamide complex cooled to −30° to −35° C. and the mixture was stirred at −30° to −35° C. for 5 hours and was then poured into a mixture of 80 ml of concentrated ammonium hydroxide containing 160 g of ice. The mixture was stirred for 15 minutes and was vacuum filtered. The product was washed with water until the wash water was neutral and dried to obtain 15.6 g of raw product. The latter was added to 25 volumes of acetone containing 20% of water and the mixture was refluxed under an inert atmosphere in the presence of 1.56 g of activated carbon for 30 minutes and was filtered through diatomaceous silica. The filtrate was concentrated, iced and vacuum filtered and the recovered product was washed twice with 15 ml of acetone containing 60% ice water and dried to obtain 4.37 g of raw product. The latter was dissolved in 800 ml of methylene chloride and 0.5 g of magnesium silicate were added thereto. The mixture was stirred under an inert atmosphere at 20° C. for one hour and was filtered. The filtrate was washed twice with 10 ml of methylene chloride and was evaporated to dryness. The residue was taken up in 20 volumes of dimethoxypropane and the mixture was refluxed and filtered hot. The filtrate was concentrated, ice and vacuum filtered and the product was washed twice with 10 ml of iced dimethoxypropane and dried to obtain 3.19 g of 9α-fluoro-17α-phenyl-$\Delta^4$-androstene-11β,17β-diol-3-one melting at 240° C. and having a specific rotation of $[\alpha]_D^{20}=+93°\pm3°$ (c=0.5% in chloroform). Treatment of the mother liquors yielded another 2.53 g of the said product.

Analysis: $C_{25}H_{31}O_3F$; molecular weight=398.5. Calculated: %C 75.35; %H 7.84; %F 4.76. Found: %C 75.0; %H 8.1; %F 4.6.

IR Spectrum (chloroform): absorption at 1665 cm$^{-1}$ (C=O); at 1625 cm$^{-1}$ (C=C); at 1493 cm$^{-1}$ (aromatic); and at 3610 and 3580 cm$^{-1}$ (OH).

| UV Spectrum (ethanol): | | |
| --- | --- | --- |
| Max at 216–217 nm | $E_1^1 = 310$ | |
| Max. at 238–239 nm | $E_1^1 = 408$ | $\epsilon = 16,300$ |
| Inflex. towards 258 nm | $E_1^1 = 5$ | |
| Inflex. towards 320 nm | $E_1^1 = 2$ | |

EXAMPLE 10

9α-fluoro-17α-phenyl-$\Delta^{1,4}$-androstadiene-11β,17β-diol-3-one 2050 ml of a solution buffered at a pH of 7 as in Example 7 was heated to 32° C. with stirring while bubbling air therethrough and a solution of 2.25 g of 9α-fluoro-17α-phenyl-$\Delta^4$-androstene-11β,17β-diol-3-one in 122 ml of methanol was added thereto. 15 g of diatomaceous silica and 15 g of arthrobacter simplex (powdered ATCC 6946) were added thereto and the operation was repeated after 25 hours of operation and again after 116 hours of reaction. During each addition, the pH was adjusted to 7 with a saturated aqueous monobasic potassium phosphate solution and after 187 hours of reaction, the decanted aqueous phase was extracted twice with methylene chloride. The mixture was vacuum filtered and the aqueous filtrate was extracted twice with ethyl acetate. The combined organic phases were dried and evaporated to dryness under reduced pressure and the residue was chromatographed over silica gel. The product was eluted with a 100-5 chloroform-methanol mixture and was crystallized from a methylene chloride-isopropyl ether mixture to obtain 1.22 g of pure 9α-fluoro-17α-phenyl-Δ$^{1,4}$-androstadiene-11β,17β-diol-3-one melting at 268° C. and having a specific rotation of [α]$_D^{20}$ = +95° (c=0.5% in ethanol). Treatment of the mother liquors yielded another 0.23 mg of the said product.

Analysis: C$_{25}$H$_{29}$O$_3$F: molecular weight=396.48. Calculated: %C 75.72; %H 7.37; %F 4.79. Found: %C 75.9; %H 7.5; %F 4.7.

IR Spectrum: absorption at 3608 and 3590 cm$^{-1}$ (OH); at 1667 cm$^{-1}$ (C=O); at 1627 and 1609 cm$^{-1}$ (C=C); at 890 cm$^{-1}$ (C—H); and at 1502 cm$^{-1}$ (aromatic).

| UV Spectrum: | | |
|---|---|---|
| Max. at 216 nm | $E_1^1 = 330$ | $\epsilon = 13,000$ |
| Inflex. towards 219 nm | $E_1^1 = 325$ | |
| Max. at 237–238 nm | $E_1^1 = 375$ | $\epsilon = 14,900$ |

EXAMPLE 11
9α-fluoro-17α-(3-trifluoromethylphenyl)-Δ$^4$-androstene-11β,17β-diol-3-one

STEP A:
9β,11β-epoxy-17α-(3-trifluoromethylphenyl)-Δ$^4$-androstene-11β-ol-3-one 357 ml of a hexane solution titering 2.1 moles/l of butyllithium were added over 10 minutes to 357 ml of anhydrous ether and a solution of 165 g of 3-trifluoromethyl-bromobenzene in 330 ml of ether were added thereto at 5° C. over 110 minutes. The mixture was stirred for 2 hours at 5° C. and the temperature was permitted to rise to room temperature over 3 hours to obtain a lithium containing solution titering 0.5 moles/l.

212 ml of the said solution were heated to reflux and a solution of 8.7 g of 3-ethoxy-9β,11β-epoxy-Δ$^{3,5}$-androstadiene-17-one in 103 ml of anhydrous ether was added thereto. The mixture was refluxed for one hour and alternate successive protonations were effected by the following steps: addition of 226 ml of ether saturated with water, refluxing with stirring for 5 minutes, addition of 212 ml of lithium containing solution, refluxing with stirring for one hour, addition of 226 ml of ether saturated with water, refluxing with stirring for 5 minutes, addition of 424 ml of lithium containing solution and refluxing with stirring for 15 hours. The mixture was cooled to 10° C. and 100 ml of a saturated aqueous ammonium chloride solution was added thereto. The decanted organic phase was washed with water and water saturated with sodium chloride, was dried and evaported to dryness to obtain 48 g of 3-ethoxy-9β,11β-epoxy-17α-(3-trifluoromethylphenyl)-Δ$^{3,5}$-androstadiene-17β-ol.

A mixture of the said product, 480 ml of ethanol and 48 ml of N sulfuric acid was heated at 60° C. with stirring under an inert atmosphere for 30 minutes and after cooling to 10° C., the mixture was neutralized with a saturated aqueous sodium bicarbonate solution. The decanted aqueous phase was added to 500 ml of methylene chloride and the organic phase was washed with a saturated aqueous sodium chloride solution, was dried and evaporated to dryness to obtain 39 g of raw product. The latter was chromatographed over silica gel and was eluted with a 7-3 benzene-ethyl acetate mixture. The product was added to 150 ml of isopropyl ether and the mixture was vacuum filtered. The product was washed with isopropyl ether and dried to obtain 9.1 g of 9β,11β-epoxy-17α-(3-trifluoromethylphenyl)-Δ$^4$-androstene-17Δ-ol-3-one melting at 146° C.

IR Spectrum (chloroform): absorption at 3605 and 3590 cm$^{-1}$ (OH); at 1485 cm$^{-1}$ (aromatic); and at 1328, 1167 and 1128 cm$^{-1}$ (CF$_3$).

| UV Spectrum (ethanol): | | |
|---|---|---|
| Inflex towards 218 nm | $E_1^1 = 200$ | |
| Max. at 243 nm | $E_1^1 = 287$ | $\epsilon = 12,800$ |
| Inflex. towards 270 nm | $E_1^1 = 37$ | |

STEP B: 9α-fluoro-17α-(3-trifluoromethylphenyl)-Δ$^4$-andros-tene-11β,17β-diol-3-one 9 g of the product of Step A were added over 15 minutes to 18 ml of a HF-dimethylformamide complex cooled to −35° C. and after stirring the mixture for 10 minutes 4.5 ml of the complex were added. The mixture was stirred for 30 minutes and was then poured into a mixture of 500 ml of ice water and 54 ml of ammonium hydroxide and the mixture was stirred for 30 minutes and was vacuum filtered. The product was washed with water until the wash water was neutral and was dried to obtain 9.65 g of raw product. The latter was chromatographed over silica gel and was eluted with a 1—1 benzene-ethyl acetate mixture. The product was added to 50 ml of isopropyl ether and the mixture was iced and vacuum filtered. The product was washed with isopropyl ether and dried and then was dissolved in 30 ml of methylene chloride. The solution was filtered hot and was concentrated, iced and vacuum filtered. The product was washed with isopropyl ether and was dried to obtain 4.34 g of 9α-fluoro-17α-(3-trifluoromethylphenyl)-Δ$^4$-androstene-11β,17β-diol-3-one melting at 254° C. and having a specific rotation of [α]$_D^{20}$= +94.5°±2.5° (c=0.5% in ethanol).

Analysis: C$_{26}$H$_{30}$O$_3$F$_4$; molecular weight=466.50. Calculated: %C 66.93; %H 6.48; %F 16.29. Found: %C 67.7; %H 6.6; %F 16.

IR Spectrum (chloroform): absorption at 3614 and 3594 cm$^{-1}$; (OH); at 1664 cm$^{-1}$ (C=O); and at 1624 cm$^{-1}$ (C=C).

| UV Spectrum (ethanol): | | |
|---|---|---|
| Inflex. towards 224 nm | $E_1^1 = 270$ | |
| Max. at 240 nm | $E_1^1 = 350$ | $\epsilon = 16,300$ |
| Infex. towards 270 nm | $E_1^1 = 17$ | |

EXAMPLE 12
9α-fluoro-17α-benzyl-Δ$^4$-androstene-11β,17β-diol-3-one

STEP A:
9β,11β-epoxy-17α-benzyl-Δ$^4$-androstene-17β-ol-3-one

A solution of 22.75 g of dibenzyl ether in 275 ml of anhydrous ether was added at −10° C. to a mixture of 13 g of powdered lithium in 300 ml of anhydrous ether and the mixture was stirred for one hour to obtain a solution of 0.22 ml/l of benzyllithium. A solution of 7 g of 3-ethoxy-9β,11β-epoxy-Δ$^{3,5}$-androstadiene-17-one in 50 ml of anhydrous ether was added to 485 ml of the benzyllithium solution and the mixture was stirred for 2½ hours at 0° C. 50 ml of a saturated aqueous ammonium chloride solution were added thereto and the decanted organic phase was washed 3 times with 100 ml of water and was filtered. The filtrate was dried and was evaporated to dryness and the residue was taken up in 140 ml of ethanol and 10 ml of N sulfuric acid at 60° C. 100 ml of an aqueous 5% sodium bicarbonate solution were added thereto and the mixture was held at 0 to 5° C. for 15 hours and was then vacuum filtered. The product was washed with water and dried to obtain 6.36 g of 9β,11β-epoxy-17α-benzyl-Δ4-androstene-17β-ol-3-one melting at 250° C.

IR Spectrum (chloroform): absorption at 3580 and 3605 cm$^{-1}$ (OH); and at 1494 cm$^{-1}$ (aromatic).

STEP B:
9α-fluoro-17α-benzyl-Δ4-androstene-11β,17β-diol-3-one 5 g of the product of Step A were added over 15 minutes to 30 ml of a HF-dimethylformamide complex cooled to −35° C. and the solution was stirred for 4 hours and was diluted with 10 ml of the said complex. The mixture was stirred for one hour and was poured into 600 ml of ice water and 200 ml of 12 N potassium hydroxide solution. The mixture was stirred for 15 minutes and was vacuum filtered and the product was washed with water until the wash water was neutral and was dried to obtain 5.8 g of raw product. The latter was chromatographed over silica gel and was eluted with a 6-4 benzene-ethyl acetate mixture. The product was dissolved in methylene chloride and 25 ml of dimethoxypropane were added thereto. The mixture was filtered and the methylene chloride was distilled. The mixture was cooled and was vacuum filtered and the product was washed with iced dimethoxypropane and dried to obtain 2.49 g of 9α-fluoro-17α-benzyl-Δ4-androstene-11β,17β-diol-3-one melting at 218° C. and having a specific rotation of $[\alpha]_D^{20} = +50.5°\pm2.5°$ (c=0.6% in chloroform).

Analysis: $C_{26}H_{33}O_3F$: molecular weight=412.54. Calculated: %C 75.69; %H 8.06; %F 4.60. Found: %C 75.8; %H 7.9; %F 4.3.

IR Spectrum (chloroform): absorptions at 1663 cm$^{-1}$ (C=O); at 1620, 1603 and 1493 cm$^{-1}$ (C=C); and at 3610 and 3580 cm$^{-1}$ (OH).

| UV Spectrum (ethanol): | | |
|---|---|---|
| Max. = 218 nm | $E_1^1$ = 290 | |
| Max. = 238 nm | $E_1^1$ = 400 | ε = 16,800 |

EXAMPLE 13

Tablets were prepared containing 5 mg or 25 mg of 17α-o-hydroxyphenyl-Δ$^{1,4}$-androstadiene-11β,17β-diol-3-one and sufficient excipient of talc, starch and magnesium stearate

PHARMACOLOGICAL DATA

Anti-inflammatory Activity

The anti-inflammatory activity was determined by the classical granuloma test of Meier et al [Experientia Vol. 6 (1950), p. 469] with conventional female rats of the Wistar strain weighing between 100 and 110 g. Two 10 mg pellets of cotton were implanted under the thorax skin and the test compound was orally administered twice a day for 2 days and 16 hours after the last administration or the third day, the animals were killed and the pellets together with the formed granuloma tissue were weighed fresh and after drying at 60° C. for 18 hours. The granuloma weight is obtained after substraction of the initial cotton weight. The skin of the thymus was taken at the same time to determine the thymolytic activity of the product. The results expressed as DA$_{50}$ (that dose which inhibits the granuloma by 50% and the dose which causes a thymus involution of 50%) were 3 mg/kg in the granuloma test and 7 mg/kg for the thymus test.

Various modifications of the products and methods of the invention may be made without departing from the spirit of scope thereof and it should be understood that the invention is to be limited only as defined in the appended claims.

We claim:
1. A compound of the formula

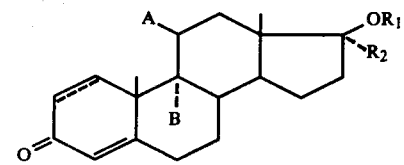

wherein $R_1$ is selected from the group consisting of hydrogen and acyl of an organic carboxylic acid of 1 to 18 carbon atoms, $R_2$ is selected from the group consisting of optionally substituted phenyl and benzyl and optionally substituted heterocyclic selected from the group consisting of furyl, thienyl, pyridyl and pyrimidyl, the optional substituents being selected from the group consisting of hydroxy, alkyl and alkoxy of 1 to 4 carbon atoms, halogens and —CF$_3$, the dotted line in the A ring indicates an optional Δ$^{1(2)}$-double bond and A may be oxo and B is hydrogen or A is β—OH and B is hydrogen or halogen or A and B form a Δ$^{9(11)}$-double bond.

2. A compound of claim 1 wherein $R_2$ is selected from the group consisting of phenyl and benzyl optionally substituted with —OH or —CF$_3$.

3. A compound of claim 1 wherein $R_1$ is hydrogen.

4. A compound of claim 1 wherein A is oxo and B is hydrogen.

5. A compound of claim 1 wherein A is β—OH and B is hydrogen.

6. A compound of claim 1 wherein A is β—OH and B is halogen.

7. A compound of claim 1 wherein A and B form a Δ$^{9(11)}$-double bond.

8. A compound of claim 1 wherein the A ring has a Δ$^{1(2)}$-double bond.

9. A comound of claim 1 wherein A ring does not have a Δ$^{1(2)}$-double bond.

10. A compound of claim 1 which is 17α-o-hydroxyphenyl -Δ$^{1,4}$-androstadiene-11β,17β-diol-3-one.

11. A compound of claim 1 which is 17β-o-hydroxyphenyl -Δ$^4$-androstene-17β-ol-3,11-dione.

12. A compound of claim 1 which is 17α-o-hydroxyphenyl -Δ$^4$-androstene-11β,17β-diol-3-one.

13. A compound of claim 1 which is 17α-phenyl-Δ$^{4,9(11)}$- androstadiene-17β-ol-3-one.

14. A compound of claim 1 which is 17α-o-hydroxyphenyl- Δ$^{4,9(11)}$-androstadiene-17β-ol-3-one.

15. A compound of claim 1 which is 9α-fluoro-17α-o-hydroxyphenyl-Δ⁴-androstene-11β,17β-diol-3-one.

16. A compound of claim 1 which is 9α-fluoro-17α-o-hydroxyphenyl-Δ¹,⁴-androstadiene-11β,17β-diol-3-one.

17. A compound of claim 1 which is 9α-bromo-17α-phenyl-Δ⁴-androstene-11β,17β-diol-3-one.

18. A compound of claim 1 which is 9α-fluoro-17α-phenyl-Δ⁴-androstene-11β,17β-diol-3-one.

19. A compound of claim 1 which is 9α-fluoro-17α-phenyl-Δ¹,⁴-androstadiene-11β,17β-diol-3-one.

20. A compound of claim 1 which is 9α-fluoro-17α-(3-trifluoromethylphenyl)-Δ⁴-androstene-11β,17β-diol-3-one.

21. A compound of claim 1 which is 9α-fluoro-17α-benzyl-Δ⁴-androstene-11β,17β-diol-3-one.

22. A process for the preparation of a compound of claim 1 comprising reacting a compound of the formula

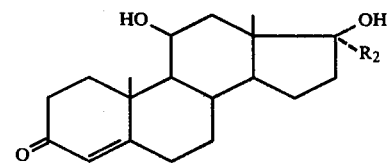

wherein AlK is alkyl of 1 to 6 carbon atoms and X is oxo and Y is hydrogen or X and Y form a Δ⁹⁽¹¹⁾-double bond with a compound of the formula R₂-Li wherein R₂ has the definition of claim 1 and then with a hydrolysis acid agent selected from the group consisting of hydrochloric acid, sulfur acid, acetic acid, citric acid and p-toluene sulfonic acid to obtain a compound of the formula

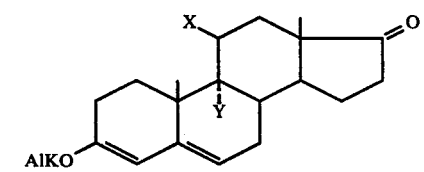

which may when X is oxo and Y is hydrogen be reacted with an alkyl orthoformate in an acid medium and then with a reducing agent followed by acid hydrolysis to obtain a compound of the formula

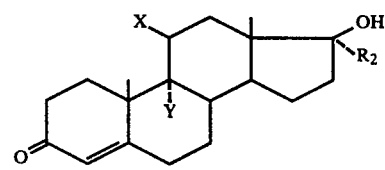

or when X and Y are a Δ⁹⁽¹¹⁾-double bond be reacted with N-bromosuccinimide in the presence of perchloric acid to obtain a compound of the formula

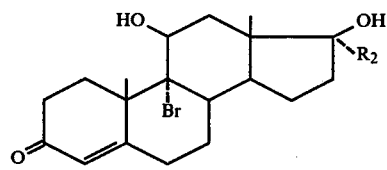

which may be reacted with a basic agent selected from the group consisting of alkali metal hydroxides and alkali metal alcoholates to obtain a compound of the formula

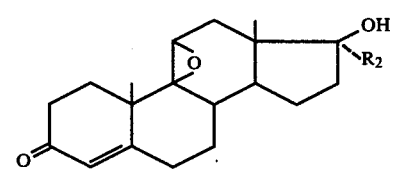

which is then reacted with H-Hal wherein Hal is chlorine or fluorine to obtain a compound of the formula

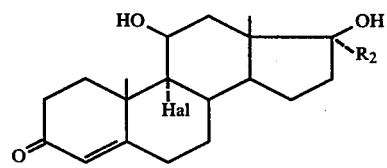

and the compounds of formulae I$_A$, I$_B$, I$_C$ and I$_D$ may be reacted with a deshydrogenation agent to obtain the corresponding Δ¹,⁴ compounds and the compounds of formula I wherein R₁ is hydrogen may be reacted with a selective esterification agent to obtain the corresponding compound of formula I wherein R₁ is acyl.

23. A process for the preparation of a compound of the formula

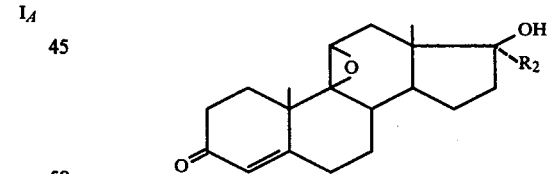

wherein R₂ is selected from the group consisting of optionally substituted phenyl and benzyl and optionally substituted heterocyclic selected from the group consisting of furyl, thienyl, pyridyl and pyrimidyl, the optional substituents being selected from the group consisting of hydroxy, alkyl and alkoxy of 1 to 4 carbon atoms, halogens and —CF₃ by reacting a compound of the formula

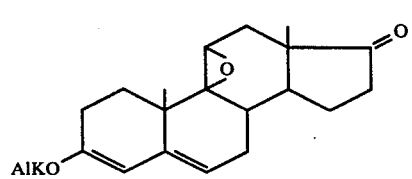

wherein AlK is alkyl of 1 to 6 carbon atoms with a compound of the formula LiR$_2$ and then with an acid hydrolysis agent selected from the group consisting of hydrochloric acid, sulfuric acid, acetic acid, citric acid and p-toluene sulfonic acid.

24. An anti-inflammatory composition comprising an anti-inflammatorily effective amount of at least one compound of claim 1 and an excipient.

25. A composition of claim 24 wherein the compound is 17α-o-hydroxyphenyl-Δ$^{1,4}$-androstadiene-11β,17β-diol-3-one.

26. A method of relieving inflammation in warm-blooded animals comprising administering to warm-blooded animals an anti-inflammatorily effective amount of at least one compound of claim 1.

27. A method of claim 26 wherein R$_2$ is selected from the group consisting of phenyl and benzyl optionally substituted with —OH or —CF$_3$.

28. A method of claim 26 wherein R$_1$ is hydrogen.

29. A method of claim 26 wherein A is oxo and B is hydrogen.

30. A method of claim 26 wherein A is β—OH and B is hydrogen.

31. A method of claim 26 wherein A is β—OH and B is halogen.

32. A method of claim 26 wherein A and B form a Δ$^{9(11)}$-double bond.

33. A method of claim 26 wherein A ring has a Δ$^{1(2)}$-double bond.

34. A method of claim 26 wherein A ring does not have a Δ$^{1(2)}$-double bond.

35. A method of claim 26 which is 17α-o-hydroxyphenyl-Δ$^{1,4}$-androstadiene-11β,17β-diol-3-one.

36. A compound selected from the group consisting of 3-alkoxy-Δ$^{3,5,9(11)}$-androstatriene-17-ones and 3-alkoxy-9β,11β-epoxy-Δ$^{3,5}$-androstadiene-17-ones wherein the alkoxy has 1 to 6 carbon atoms.

37. A compound of claim 36 selected from the group consisting of 3-ethoxy-9β,11β-epoxy-Δ$^{3,5}$-androstadiene-17-one and 3-ethoxy-Δ$^{3,5,9(11)}$-androstatriene-17-one.

* * * * *

UNITED STATES PATENT AND TRADEMARK OFFICE
CERTIFICATE OF CORRECTION

PATENT NO. : 4,203,981
DATED : May 20, 1980
INVENTOR(S) : Andre Pierdet, Vesperto Torelli and Roger Deraedt It is certified that error appears in the above—identified patent and that said Letters Patent is hereby corrected as shown below:

| Col. | Line | | |
|---|---|---|---|
| | | Abstract | "Δ-OH" should be —β-OH— |
| 3 | 64 | | "$66^{3,5,9(11)}$" should be —$\Delta^{3,5,9(11)}$— |
| 4 | 28 | | "17β" should be —17α— |
| 9 | 43 | | "benzne" should be —benzene— |
| 11 | 25 | | "Be" should be —Bè— |
| 14 | 7 | | "17Δ" should be —17β— |
| 14 | 19 | | "andros-tene" should be —androstene— |
| 16 | Claim 11 | | "17β" should be —17α— |

Signed and Sealed this

Thirtieth Day of December 1980

[SEAL]

Attest:

SIDNEY A. DIAMOND

Attesting Officer    Commissioner of Patents and Trademarks